United States Patent
Hashimoto

(10) Patent No.: US 12,138,141 B2
(45) Date of Patent: Nov. 12, 2024

(54) METHOD FOR PRODUCING ABSORBENT ARTICLE

(71) Applicant: LIVEDO CORPORATION, Ehime (JP)

(72) Inventor: Atsushi Hashimoto, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 728 days.

(21) Appl. No.: 17/428,042

(22) PCT Filed: Feb. 5, 2020

(86) PCT No.: PCT/JP2020/004351
§ 371 (c)(1),
(2) Date: Aug. 3, 2021

(87) PCT Pub. No.: WO2020/166449
PCT Pub. Date: Aug. 20, 2020

(65) Prior Publication Data
US 2022/0104972 A1 Apr. 7, 2022

(30) Foreign Application Priority Data
Feb. 15, 2019 (JP) .................. 2019-025381

(51) Int. Cl.
*A61F 13/15* (2006.01)
*A61F 13/534* (2006.01)
(Continued)

(52) U.S. Cl.
CPC ...... *A61F 13/15617* (2013.01); *A61F 13/534* (2013.01); *A61L 15/28* (2013.01);
(Continued)

(58) Field of Classification Search
CPC .......... A61L 15/28; A61L 15/44; A61L 15/48; A61F 13/15617; A61F 13/534;
(Continued)

(56) References Cited

U.S. PATENT DOCUMENTS 7,076,848 B2 * 7/2006 Ames ..................... D04H 1/60
28/282
2003/0105442 A1 6/2003 Johnston et al.
(Continued)

FOREIGN PATENT DOCUMENTS

| CN | 1736355 | 2/2006 |
| CN | 101394995 | 3/2009 |

(Continued)

OTHER PUBLICATIONS

International Search Report (ISR) issued Apr. 21, 2020 in International (PCT) Application No. PCT/JP2020/004351.
(Continued)

*Primary Examiner* — Michael P Wieczorek
(74) *Attorney, Agent, or Firm* — Wenderoth, Lind & Ponack, L.L.P.

(57) ABSTRACT

[Object] To provide a method for producing an absorbent article comprising a fiber assembly layer of a cellulose acetate fiber, which can sufficiently apply a drug to the cellulose acetate fiber.
[Solution] A method for producing an absorbent article, wherein the absorbent article comprises: a fiber assembly layer including a cellulose acetate fiber, and a member including a water absorbent fiber and directly disposed on the fiber assembly layer, and the method comprises: a first step of opening a cellulose acetate tow and collecting a cellulose acetate fiber to form a fiber assembly layer, a second step of spreading a fiber solvent on the fiber assembly layer and drying the fiber assembly layer; a third step of
(Continued)

spreading a drug aqueous solution containing an antibacterial agent and/or a deodorizer on the surface where the fiber solvent has been spread of the fiber assembly layer; and a fourth step of mounting the member on the surface where the drug aqueous solution has been spread of the fiber assembly layer.

20 Claims, 1 Drawing Sheet

(51) Int. Cl.
  *A61L 15/28* (2006.01)
  *A61L 15/44* (2006.01)
  *A61L 15/48* (2006.01)
(52) U.S. Cl.
  CPC ............... *A61L 15/44* (2013.01); *A61L 15/48* (2013.01); *A61F 2013/15837* (2013.01); *A61L 2300/00* (2013.01); *A61L 2300/21* (2013.01)
(58) Field of Classification Search
  CPC .......... A61F 13/15577; A61F 13/15634; A61F 13/15642; A61F 13/1565
  See application file for complete search history.

(56) References Cited

U.S. PATENT DOCUMENTS

| | | |
|---|---|---|
| 2006/0184149 A1 | 8/2006 | Kasai et al. |
| 2016/0199527 A1 | 7/2016 | Ota et al. |
| 2017/0020749 A1 | 1/2017 | Nakamura et al. |

FOREIGN PATENT DOCUMENTS

| | | |
|---|---|---|
| CN | 109196163 | 1/2019 |
| JP | 2001-198155 | 7/2001 |
| JP | 2014-79324 | 5/2014 |
| JP | 2015-196915 | 11/2015 |
| JP | 2016-187549 | 11/2016 |
| WO | 03/047486 | 6/2003 |

OTHER PUBLICATIONS

Office Action issued Apr. 1, 2022 in corresponding Chinese Patent Application No. 202080007116.1, with English translation.

\* cited by examiner

[Fig. 1]
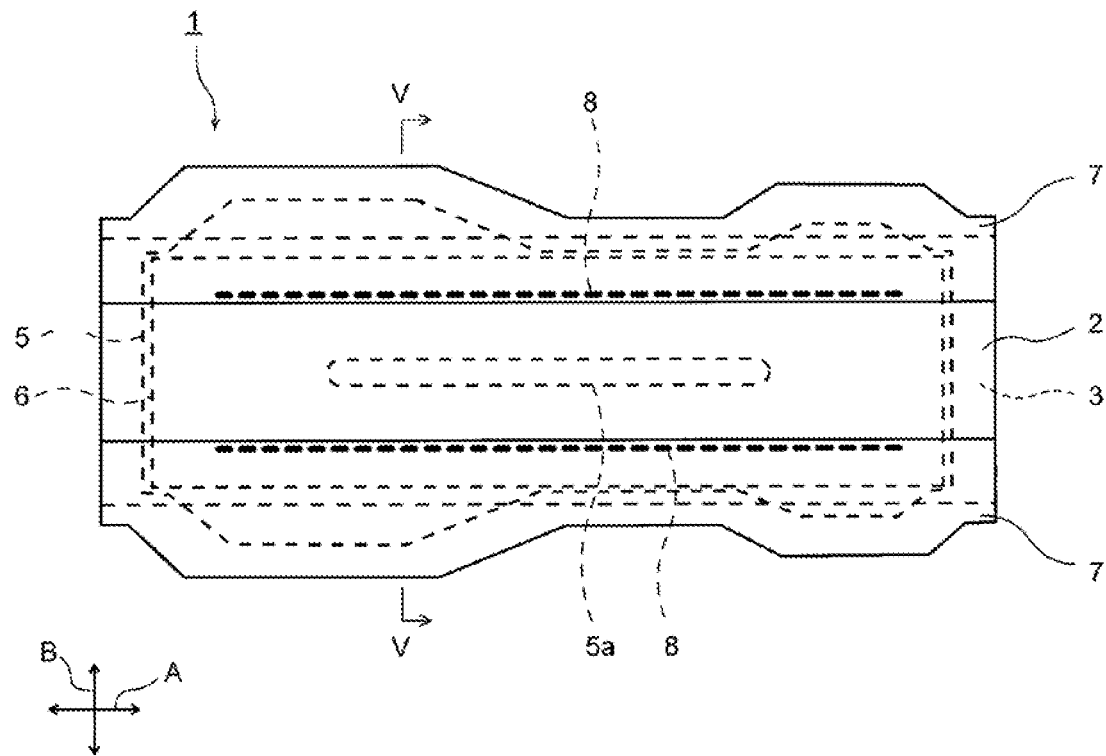
[Fig. 2]
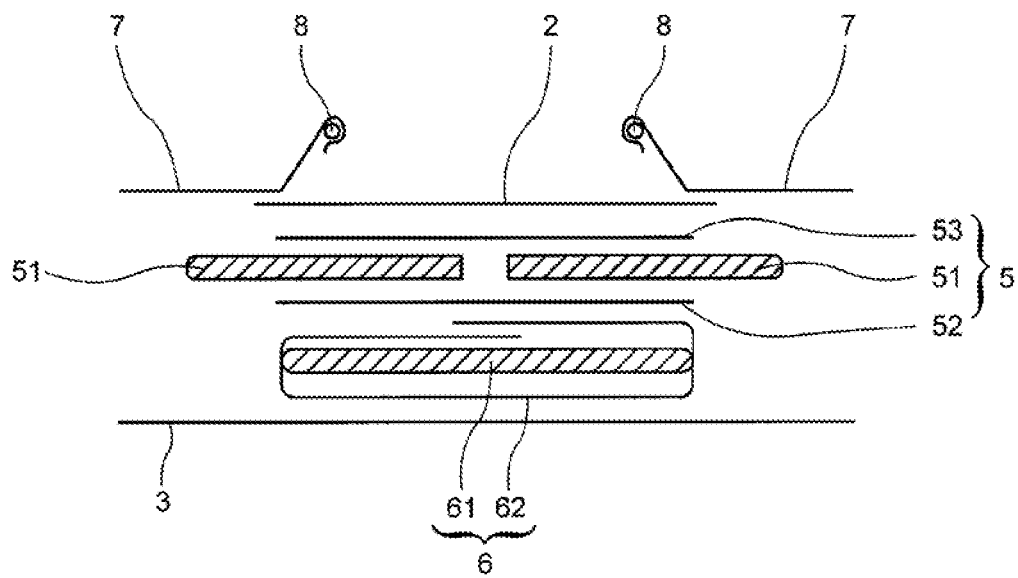

METHOD FOR PRODUCING ABSORBENT ARTICLE

FIELD OF THE INVENTION

The present invention relates to a method for producing an absorbent article comprising a fiber assembly layer of a cellulose acetate fiber.

DESCRIPTION OF THE RELATED ART

An absorbent article such as an incontinence pad, disposable diaper, and sanitary napkin comprises an absorbent body for absorbing and retaining body fluid excreted from body such as urine and menstrual blood. The absorbent body generally includes a water absorbent resin powder, and body fluid is absorbed and retained in the water absorbent resin powder inside the absorbent body.

As such absorbent article, an absorbent article comprising a cellulose acetate fiber has been proposed. For example, patent literature 1 discloses an absorbent article comprising a water absorbent layer and a diffusion layer disposed under the water absorbent layer, wherein a water absorbent resin powder having specific properties is disposed in the water absorbent layer, and the diffusion layer includes a cellulose acetate fiber (refer to paragraphs 0124 to 0137 of patent literature 1).

In addition, usage of a cellulose acetate fiber as a deodorizer has been proposed. For example, patent literature 2 discloses a deodorizer material comprising a cellulose diacetate fiber and condensed tannin (refer to paragraphs 0023 and 0032 of patent literature 2).

CITATION LIST

Patent Literature

Patent literature 1: JP 2014-7024 A
Patent literature 2: JP 2016-187549 A

SUMMARY OF THE INVENTION

Problem to be Solved by the Invention

As described above, conventionally, a deodorizer is applied to a fiber assembly layer of a cellulose acetate fiber. Since the cellulose acetate fiber has low affinity for water, when a drug aqueous solution is dispersed on the fiber assembly layer of the cellulose acetate fiber, a certain time is required for the drug aqueous solution to be taken into the fiber assembly layer. Therefore, in the production of an absorbent article, when a member including a water absorbent fiber is laminated on the fiber assembly layer of the cellulose acetate fiber on which the drug aqueous solution has been dispersed, the drug aqueous solution tends to migrate to the member including the water absorbent fiber. As a result, there was a problem that the drug cannot be sufficiently applied to the fiber assembly layer of the cellulose acetate fiber.

The present invention has been made in view of the above circumstances, and an object of the present invention is to provide a method for producing an absorbent article comprising a fiber assembly layer of a cellulose acetate fiber, which can sufficiently apply a drug to the cellulose acetate fiber.

Solution to Solve Problem

The present invention provides a method for producing an absorbent article, wherein the absorbent article comprises: a fiber assembly layer including a cellulose acetate fiber, and a member including a water absorbent fiber and directly disposed on the fiber assembly layer, and the method comprises: a first step of opening a cellulose acetate tow and collecting a cellulose acetate fiber to form a fiber assembly layer; a second step of spreading a fiber solvent on the fiber assembly layer and drying the fiber assembly layer; a third step of spreading a drug aqueous solution containing an antibacterial agent and/or a deodorizer on the surface where the fiber solvent has been spread of the fiber assembly layer; and a fourth step of mounting the member on the surface where the drug aqueous solution has been spread of the fiber assembly layer.

The fiber solvent is a solvent that can dissolve the cellulose acetate fiber. Such fiber solvent spread on the fiber assembly layer can dissolve the surface of the cellulose acetate fiber. Thus, spreading the fiber solvent on the fiber assembly layer and drying the fiber assembly layer allows the portion where the fibers are in contact with each other in the layer to be welded. Welding a part of the fiber can suppress the decrease in the distance between the fibers when spreading the drug aqueous solution, and further speed up the permeation of the drug aqueous solution, Therefore, the spread drug aqueous solution immediately disperses in the fiber assembly layer, and even if the member including the water absorbent fiber is mounted directly on the fiber assembly layer, the migration of the drug aqueous solution to the member is suppressed. Thus, the drug can be sufficiently applied to the fiber assembly layer.

Effect of the Invention

According to the present invention, the drug can be sufficiently applied to the cellulose acetate fiber in the method for producing the absorbent article comprising the fiber assembly layer of the cellulose acetate fiber.

BRIEF DESCRIPTION OF THE DRAWINGS

FIG. 1 is a planar view of one example of an absorbent article; and

FIG. 2 is a schematic cross-sectional view along line V-V in FIG. 1.

DESCRIPTION OF THE PREFERRED EMBODIMENT

The present invention provides a method for producing an absorbent article, wherein the absorbent article comprises: a fiber assembly layer including a cellulose acetate fiber, and a member including a water absorbent fiber and directly disposed on the fiber assembly layer.

[Absorbent Article]

The absorbent article comprises: a liquid permeable top sheet, a liquid impermeable back sheet, and an absorbent body disposed between the top sheet and the back sheet and comprising a water absorbent resin powder, wherein the fiber assembly layer is disposed between the back sheet and the absorbent body. The fiber assembly layer is disposed for the purpose of imparting cushioning property to the absorbent article, and for the purpose of absorbing and retaining the body fluid reaching the external surface of the absorbent body as well.

(Fiber Assembly Layer)

The fiber assembly layer includes the cellulose acetate fiber. The cellulose acetate fiber is a semisynthetic fiber obtained by esterifying cellulose with acetate acid.

Examples of the cellulose acetate fiber include a cellulose diacetate fiber (degree of esterification: 2.22 or more and less than 2.76) having 74% or more and less than 92% of the hydroxy groups of the cellulose being esterified with acetate acid, and a cellulose triacetate fiber (degree of esterification: 2.76 or more) having 92% or more of the hydroxy groups of the cellulose being esterified with acetate acid. The cellulose diacetate fiber is preferable. It is noted that the degree of esterification is an average number of the hydroxy groups substituted by an acetyl group per glucose unit in the cellulose.

The fineness of the cellulose acetate fiber (monofilament) is preferably 0.1 dtex or more, more preferably 0.8 dtex or more, and even more preferably 1.5 dtex or more, and is preferably 16 dtex or less, more preferably 12 dtex or less, and even more preferably 8 dtex or less. If the fineness is 0.1 dtex or more, the fiber assembly layer has more enhanced cushioning property, and if the fineness 16 dtex or less, the fiber assembly layer has better texture.

The cross-sectional shape of the cellulose acetate fiber is not particularly limited, and may be a circular shape, elliptical shape, triangular shape, L shape, Y shape, X shape, W shape, eight-foil shape, flat shape (such as boomerang shape, wave shape, cocoon shape and cuboidal shape), polygonal shape such as dog bone shape, multifoil shape, hollow shape, or irregular shape. From the standpoint of enhancing the dryness after absorbing the body fluid, the cross-sectional shape of the cellulose acetate fiber is preferably the circular shape or elliptical shape.

The fiber assembly layer may further include other fiber than the cellulose acetate fiber. In this case, the amount of the cellulose acetate fiber in the fiber assembly layer is 50 mass % or more, preferably 70 mass % or more, more preferably 90 mass % or more. It is noted that the fiber assembly layer most preferably consists of the cellulose acetate fiber. Examples of the other fiber include a cellulose fiber, polyester fiber, polyolefin fiber, polyamide fiber, polyvinyl alcohol fiber, and acrylic fiber.

The mass per unit area of the fiber assembly layer is preferably 20 g/m$^2$ or more, more preferably 30 g/m$^2$ or more, and even more preferably 40 g/m$^2$ or more, and is preferably 150 g/m$^2$ or less, more preferably 135 g/m$^2$ or less, and even more preferably 120 g/m$^2$ or less. If the mass per unit area is 20 g/m$^2$ or more, the fiber assembly layer has more enhanced cushioning property, and if the mass per unit area is 150 g/m$^2$ or less, the fiber assembly layer has better texture.

The thickness of the fiber assembly layer is preferably 1 mm or more, more preferably 1.5 mm or more, and even more preferably 2 mm or more, and is preferably 20 mm or less, more preferably 17.5 mm or less, and even more preferably 15 mm or less. If the thickness is 1 mm or more, the fiber assembly layer has more enhanced cushioning property, and if the thickness is 20 mm or less, the absorbent article is not excessively bulky, and has better wearing feeling. The thickness of the fiber assembly layer is measured with a thickness gage (SM-130, available from TECLOCK Co., Ltd.) in a final pressure of 2.2 N or less. An anvil and a gauge head used in the measurement have a flat surface which is in contact with the measuring object and has a diameter of 10 mm.

The fiber assembly layer preferably has a low-density region and a high-density region having a higher density than the low-density region, in the width direction. It, is preferable that the central region in the width direction of the fiber assembly layer is the low-density region, and the regions of the fiber assembly layer on the outer sides in the width direction of the low-density region are the high-density regions. Specifically, when one edge of the fiber assembly layer is 0%, another edge of the fiber assembly layer is 100%, and the central part in the width direction of the fiber assembly layer is 50%, the low-density region preferably exists in a range from 25% to 75%, more preferably exists in a range from 35% to 65%.

When the fiber assembly layer has the low-density region and the high-density region, the density ratio of the high-density region to the low-density region (density of high-density region/density of low-density region) is preferably 1.2 or more, more preferably 1.3 or more, and even more preferably 1.4 or more, and is preferably 3 or less, more preferably 2.5 or less, and even more preferably 2 or less. If the density ratio is 1.2 or more, fiber amount can be decreased in the central part in the width direction of the fiber assembly layer, that is the urination position, thereby enhancing the permeation of body fluid, and if the density ratio is 3 or less, the edge regions of the fiber assembly layer become less bulky.

The contact points of the constituent fibers in the fiber assembly layer are fixed to each other. If the contact points of the fibers are fixed to each other, the fiber assembly layer has further enhanced cushioning property, and has maintained voids between the fibers when the body fluid is taken therein, thereby enhancing the body fluid absorbing s peed.

The fiber assembly layer preferably has a first region where the fixed degree of the constituent fibers is low, and a second region where the fixed degree of the constituent fibers is higher than that of the first region. It is preferable that the central region in the width direction of the fiber assembly layer is the second region, and the regions on the outer sides in the width direction of the second region of the fiber assembly layer are the first regions. Specifically, when one edge of the fiber assembly layer is 0%, another edge of the fiber assembly layer is 100%, and the central part in the width direction of the fiber assembly layer is 50%, the second region preferably locates in a range from 10% to 90%, The higher fixed degree of the fibers in the central part in the width direction can increase the permeation speed of body fluid in the part corresponding to the urination position of the wearer. The fixed degree of the constituent fibers can be adjusted by increasing or decreasing the amount of the fiber solvent which will be described later.

It is noted that the second region preferably includes the low-density region.

The fiber constituting the fiber assembly layer is provided with either of or both of the antibacterial agent and the deodorizer.

The antibacterial agent is not particularly limited, as long as the agent imparts the antibacterial activity to the cellulose acetate fiber, and examples thereof include an organic acid, Examples of the organic acid include butanoic acid, valeric acid, caproic acid, enanthic acid, caprylic acid, pelargonic acid, capric acid, lauric acid, myristic acid, palmitic acid, margaric acid, stearic acid, arachidic acid, lactic acid, myristoleic acid, palmitoleic acid, oleic acid, elaidic acid, vaccenic acid, oxalic acid, malonic acid, succinic acid, glutaric acid, adipic acid, pimelic acid, suberic acid, azelaic acid, sebacic acid, malic acid, tartaric acid, citric acid, fumaric acid, maleic acid, glutaconic acid, itaconic acid, 2-methylene glutaric acid, aconitic acid, benzoic acid, 2-naphthoic acid, gallic acid, phthalic acid, isophthalic acid, and dehydroacetic acid. Among them, fumaric acid, dehydroacetic acid, and benzoic acid are preferable.

The solubility of the organic acid in water (25° C.) is preferably 0.1 g/100 g or more, and is preferably 10 g/100 g or less, more preferably 9 g/100 g or less, and even more preferably 8 g/100 g or less. If the solubility is 10 g/100 g or less, the organic acid adhered to the fiber slowly dissolves in the body fluid or the like, and thus the antibacterial activity thereof can be exerted for a long period of time.

The amount of the organic acid to be add is preferably 0.0001 part by mass or more, more preferably 0.001 part by mass or more, and is preferably 0.15 part by mass or less, more preferably 0.05 part by mass or less, and even more preferably 0.015 part by mass or less, with respect to 100 parts by mass of the fiber assembly layer. If the amount of the organic acid to be added is 0.0001 part by mass or more, the fiber assembly layer has more enhanced antibacterial effect, and if the amount of the organic acid is 0.15 part by mass or less, adverse effect on skin caused by the excessively high level of the organic acid can be suppressed.

Examples of the deodorizer include a polyphenol compound and cyclodextrin. As the polyphenol compound, an extract obtained from plants such as pine, hiba, Japanese cypress, cedar, tea, Japanese camellia, sasanqua, persimmon, bamboo, bamboo grass, sage, thyme, rosemary, eucalyptus, lavender, parsley, apple fruit, grape seed, mushroom and alga can be used. As the plant extract, the extract obtained from plants such as tea, Japanese camellia, sasanqua, persimmon, bamboo, bamboo grass, eucalyptus and grape seed which contain a great level of catechins and flavones are preferable, condensed tannin is more preferable.

The amount of the deodorizer to be added is preferably 0.01 part by mass or more, more preferably 0.1 part by mass or more, and even more preferably 1 part by mass or more, and is preferably 50 parts by mass or less, more preferably 30 parts by mass or less, and even more preferably 20 parts by mass or less, with respect to 100 parts by mass of the fiber assembly layer. If the amount of the deodorizer to be added is 0.01 part by mass or more, the deodorization effect is further enhanced, and if the amount of the deodorizer to be added is 50 parts by mass or less, lowering in the texture of the fiber assembly layer can be suppressed.

The antibacterial agent and the deodorizer can be applied uniformly to the whole fiber assembly layer, or be applied nonuniformly in different amounts to the fiber assembly layer. Specifically, the amount of the antibacterial agent and the deodorizer to be applied to the high-density region is preferably higher than the amount of the antibacterial agent and the deodorizer to be applied to the low-density region. In addition, the amount of the antibacterial agent and the deodorizer to be applied to the second region is preferably higher than the amount of the antibacterial agent and the deodorizer to be applied to the first region.

(Member Including Water Absorbent Fiber)

The member including the water absorbent fiber is disposed on the fiber assembly layer such that the member is in contact with the fiber assembly layer.

The water absorbent fiber is a more hydrophilic fiber than the cellulose acetate fiber, and specifically is a fiber having a SP (solubility parameter) value of more than 11.4. Examples of the water absorbent fiber include a cellulose fiber.

Examples of the member including the water absorbent fiber include a tissue paper composed of a cellulose fiber, and a water absorbent layer including a pulp fiber and a water absorbent resin powder. Examples of the combination of the fiber assembly layer and the member include a combination of the fiber assembly layer and the tissue paper wrapping the fiber assembly layer; a combination of the fiber assembly layer and the water absorbent layer directly formed on the fiber assembly layer; and a combination of the fiber assembly layer and an absorbent body (a product having the water absorbent layer wrapped with the tissue paper) directly disposed on the fiber assembly layer.

(Top Sheet)

The top sheet is disposed on a side of the absorbent article closest to the wearer to rapidly capture the body fluid from the wearer and transfer the body fluid toward the absorbent body. As the top sheet, a liquid permeable sheet material, for example, a nonwoven fabric formed of a hydrophilic fiber can be used. The nonwoven fabric used as the top sheet is, for example, a point-bonded nonwoven fabric, air-through nonwoven fabric, spunlace nonwoven fabric, or spunbond nonwoven fabric. As the hydrophilic fiber for forming these nonwoven fabrics, cellulose, rayon, cotton, and the like are usually used. It is noted that as the top sheet, a liquid permeable nonwoven fabric formed of a hydrophobic fiber (for example, polypropylene, polyethylene, polyester, and polyamide) whose surface is hydrophilized with a surfactant may be used.

(Back Sheet)

The back sheet is disposed on an outermost side of the absorbent article to prevent the body fluid or the like from leaking out. As the liquid impermeable sheet used as the back sheet, a water-repellent or liquid impermeable nonwoven fabric (for example, a spunbond nonwoven fabric, meltblown nonwoven fabric, and SMS (spunbond-meltblown-spunbond) nonwoven fabric) formed by a hydrophobic fiber (for example, polypropylene, polyethylene, polyester, polyamide, and nylon), or a water-repellent or liquid impermeable plastic film is used to prevent the body fluid reaching the liquid impermeable sheet from oozing out of the absorbent article. When the plastic film is used as the liquid impermeable sheet, a moisture permeable (air permeable) plastic film is preferably used from the standpoint of preventing the humid feeling and enhancing the wearer's comfortableness.

(Absorbent Body)

The absorbent body can absorb body fluid. The absorbent body includes at least one water absorbent layer. The water absorbent layer includes the water absorbent resin powder as the water absorbent material. The water absorbent layer may further include the water absorbent, fiber as the water absorbent material.

As the water absorbent resin powder, a water absorbent resin powder used in the conventional absorbent article can be used. The water absorbent resin powder is preferably, but not particularly limited to, a crosslinked polymer having acrylic acid as a constituent component and having carboxyl groups being at least partially neutralized. The amount of the acrylic acid component constituting the crosslinked polymer is preferably 50 mass % or more, more preferably 90 mass % or more, and even more preferably 95 mass % or more, and is preferably 99 mass % or less, more preferably 97 mass % or less. If the amount of the acrylic acid component fails within the above range, the obtained water absorbent resin powder easily has the desired absorbent performance.

Examples of the cation for neutralizing at least a part of the carboxyl groups of the crosslinked polymer include, but are not particularly limited to, an alkali metal ion such as lithium, sodium and potassium; and an alkaline earth metal ion such as magnesium and calcium. Among them, at least a part of the carboxyl groups of the crosslinked polymer is preferably neutralized with a sodium ion. It is noted that the neutralization of the carboxyl groups of the crosslinked polymer can be conducted by neutralizing the carboxyl groups of the crosslinked polymer obtained by polymerization, or alternatively be conducted by using a monomer which has been neutralized in advance to form the crosslinked polymer.

The neutralization degree f the carboxyl groups of the crosslinked polymer is preferably 55 mole % or more, more preferably 60 mole % or more. If the neutralization degree is excessively low, the obtained water absorbent resin powder may have lowered absorbent performance. In addition, the upper limit of the neutralization degree is not particularly limited, and all the carboxylic groups can be neutralized. It is noted that the neutralization degree is calculated according to the following formula.

Neutralization degree (mole %)=100×[Number of moles of neutralized carboxyl groups in crosslinked polymer]/[Total number of moles of carboxyl groups in crosslinked polymer (including neutralized and unneutralized carboxyl groups)]

The water absorbent resin powder may further include an additive such as an antiseptic, fungicide, antibacterial agent, antioxidant, ultraviolet absorbent agent, coloring agent, perfuming agent, deodorizer, inorganic powder, and organic fibrous material. Examples of the water absorbent fiber include a pulp fiber, cellulose fiber, rayon, and acetate fiber.

The water absorbent layer may include a fiber base material in addition to the water absorbent resin powder. Examples of the fiber base material include a thermal bonding fiber. The thermal bonding fiber is used to enhance shape-retention. Specific examples of the thermal bonding fiber include a polyolefin fiber such as a polyethylene fiber and a polypropylene fiber, a polyester fiber, and a composite fiber. If the water absorbent material of the water absorbent layer consists of the water absorbent resin powder, the water absorbent layer can be made thin. The water absorbent layer including the fiber base material is superior in dispersibility of body fluid, (Absorbent Article)

Examples of the embodiment of the absorbent article include an embodiment comprising a liquid permeable top sheet, a liquid impermeable back sheet, and an absorbent body disposed between the top sheet and the back sheet, wherein the fiber assembly layer is disposed between the back sheet and the absorbent body, and the fiber assembly layer is wrapped with a nonwoven fabric composed of a water absorbent fiber; and an embodiment comprising a liquid permeable top sheet, a liquid impermeable back sheet, and an absorbent body disposed between the top sheet and the back sheet, wherein the fiber assembly layer is disposed between the back sheet and the absorbent body, the absorbent body includes a water absorbent layer and a nonwoven fabric wrapping the water absorbent layer and composed of a water absorbent fiber, and the absorbent body is disposed directly on the fiber assembly layer.

Next, using an incontinence pad as an example, the absorbent article will be specifically described with reference to FIGS. 1 and 2. FIG. 1 shows a planar view of an incontinence pad. FIG. 2 shows a V-V cross-sectional view of the incontinence pad in FIG. 1. It is noted that, in the figures, the arrow B indicates a width direction, the arrow A indicates a longitudinal direction, and the direction on the plane formed by the arrows A and B is a planar direction.

The incontinence pad absorbent article) 1 shown in FIGS. 1 and 2 comprises a liquid permeable top sheet 2, a liquid impermeable back sheet 3, and an absorbent body 5 and a wrapped body 6 disposed therebetween.

The absorbent body 5 is composed of a first base material 52, a second base material 53, and a water absorbent layer 51 disposed therebetween. The water absorbent layer 51 is composed of a pulp fiber and a water absorbent resin powder. The absorbent body 5 has an opening 5a at the central part in the width direction. In FIGS. 1 and 2, the example using the absorbent body 5 with a gourd shape in a planar view as the absorbent body is shown, but the embodiment of the absorbent body is not limited to this. In FIGS. 1 and 2, the absorbent body 5 is composed of the first base material 52, the second base material 53, and the water absorbent layer 51 disposed therebetween, but the second base material 53 may not be disposed so that the top sheet 2 and the water absorbent layer 51 are in direct contact. In addition, in FIGS. 1 and 2, the absorbent body 5 has the opening 5a, but the absorbent body 5 may not have an opening.

The incontinence pad 1 has the wrapped body 6 on the back sheet side of the absorbent body 5. The wrapped body 6 is composed of a fiber assembly layer 61 of a cellulose acetate fiber and a tissue paper 62 wrapping the fiber assembly layer 61. In addition, the contact points of the constituent fibers in the fiber assembly layer are fixed to each other. The antibacterial agent and/or deodorizer is supported on the fiber assembly layer of the cellulose acetate fiber.

Side sheets 7 extending along the longitudinal direction A of the incontinence pad 1 are joined to both edges of the top sheet 2 in the width direction B. The side sheet 7 is formed of a liquid impermeable plastic film, a water-repellent nonwoven fabric, or the like. A raising elastic member 8 is provided on the side sheet 7 at an inner edge of the incontinence pad 1 in the width direction. When the incontinence pad 1 is used, the inner edges of the side sheet 7 rise toward the skin of the wearer by the contracting force of the raising elastic member 8, by which side leakage of the excrement such as urine is prevented.

[Production Method]

The method for producing the absorbent article comprises: a first step of opening a cellulose acetate tow and collecting a cellulose acetate fiber to form a fiber assembly layer; a second step of spreading a fiber solvent on the fiber assembly layer and drying the fiber assembly layer; a third step of spreading a drug aqueous solution containing an antibacterial agent and/or a deodorizer on the surface where the fiber solvent has been spread of the fiber assembly layer; and a fourth step of mounting the member on the surface where the drug aqueous solution has been spread of the fiber assembly layer.

(First Step)

In the first step, the cellulose acetate tow is opened and the cellulose acetate fiber is collected to form the fiber assembly layer.

The cellulose acetate tow is a fiber bundle of cellulose acetate filaments. The cellulose acetate tow preferably has 3,000 or more filaments, more preferably has 5,000 or more filaments, and preferably has 1,000,000 or less filaments, more preferably has 900,000 or less filaments.

Examples of the method for opening the tow include a method of hanging the tow on a plurality of opening rolls and increasing the width of the tow with the progress of the tow to open the tow; a method of repeating tow tension (elongation) and tow relaxation (contraction) to open the tow; and a method of using compressed air to widen and open the tow. The opening width of the tow is not limited, but it is usually about 100 mm to 300 mm which is the width of the fiber assembly layer. In addition, the mass per unit area of the fiber assembly layer can be adjusted by adjusting the opening degree of the tow.

The fiber assembly layer may be formed directly on the back sheet, or be formed on a sheet material for enhancing shape stability. In addition, the fiber assembly layer is preferably fixed to the back sheet or sheet material with an adhesive.

The fiber assembly layer may be formed to have a uniform or nonuniform density along the width direction. For example, the fiber assembly layer can be formed such that the density of the central region in the width direction of the fiber assembly layer is lower than the density of the regions of both edges in the width direction of the fiber assembly layer.

(Second Step)

In the second step, the fiber solvent is spread on the fiber assembly layer and the fiber assembly layer is dried.

The fiber solvent is a solvent that can dissolve the cellulose acetate fiber. Such fiber solvent spread on the fiber assembly layer can dissolve the surface of the cellulose acetate fiber. Thus, spreading the fiber solvent on the fiber assembly layer and drying the fiber assembly layer allows the portion where the fibers are in contact with each other in the layer to be welded. Welding a part of the fiber can suppress the decrease in the distance between the fibers when spreading the drug aqueous solution, and further speed up the permeation of the drug aqueous solution.

Examples of the fiber solvent include triacetin. The spreading amount of the fiber solvent is preferably 0.1 $g/m^2$ or more, more preferably 0.2 $g/m^2$ or more, and even more preferably 0.5 $g/m^2$ or more, and is preferably 5 $g/m^2$ or less, more preferably 3 $g/m^2$ or less, and even more preferably 1.5 $g/m^2$ or less. If the spreading amount is 0.1 $g/m^2$ or more, the fiber solvent can be spread uniformly, and if the spreading amount is 5 $g/m^2$ or less, lowering in the texture of the fiber assembly layer can be suppressed.

The fiber solvent can be spread uniformly on the whole fiber assembly layer, or be spread nonuniformly on the fiber assembly layer. The amount per unit area of the fiber solvent spread in the central region in the width direction of the fiber assembly layer is preferably higher than the amount per unit area of the fiber solvent spread in the regions of both edges in the width direction of the fiber assembly layer. The higher amount in the central region in the width direction can increase the fixed degree of the fibers in this region, thereby suppressing the decrease in the permeation speed of the drug aqueous solution even in a case that the amount of the drug aqueous solution in the central region in the width direction is increased.

In addition, when the fiber assembly layer has uniform densities, the amount per unit area of the fiber solvent spread in the low-density part of the fiber assembly layer is preferably higher than the amount per unit area of the fiber solvent spread in the high-density part of the fiber assembly layer. Specifically, when the fiber assembly layer is formed in the first step such that the density of the central region in the width direction of the fiber assembly layer is lower than the density of the regions of both edges in the width direction of the fiber assembly layer, the amount per unit area of the fiber solvent spread in the central region in the width direction is preferably higher than the amount per unit area of the fiber solvent spread in the regions of both edges in the width direction in the second step.

(Third Step)

In the third step, the drug aqueous solution containing the antibacterial agent and/or the deodorizer is spread on the surface where the fiber solvent has been spread of the fiber assembly layer in the second step. The drug aqueous solution contains the antibacterial agent and/or the deodorizer.

The amount of the antibacterial agent in the drug aqueous solution is preferably 0.001 part by mass or more, more preferably 0.01 part by mass or more, and even more preferably 0.1 part by mass or more, and is preferably 50 parts by mass or less, more preferably 5 parts by mass or less, and even more preferably 0.5 part by mass or less, with respect to 100 parts by mass of water. If the amount of the antibacterial agent is 0.001 part by mass or more, the fiber assembly layer can express the antibacterial effect even if a small amount of the drug aqueous solution is applied, and if the amount of the antibacterial agent is 50 parts by mass or less, adverse effect on skin caused by the excessive amount of the antibacterial agent can be suppressed.

The amount of the deodorizer in the drug aqueous solution is preferably 0.01 part by mass or more, more preferably 0.1 part by mass or more, and even more preferably 1 part by mass or more, and is preferably 50 parts by mass or less, more preferably 30 parts by mass or less, and even more preferably 10 parts by mass or less, with respect to 100 parts by mass of water. If the amount of the deodorizer is 0.01 part by mass or more, the fiber assembly layer can express the deodorization effect even if a small amount of the drug aqueous solution is applied, and if the amount of the deodorizer is 50 parts by mass or less, the drug aqueous solution has lowered viscosity and thus easily permeates into the fiber assembly layer.

The drug aqueous solution preferably further contains a surfactant, Inclusion of the surfactant can speed up the permeation of the drug aqueous solution applied to the fiber assembly layer, into the fiber assembly layer. The surfactant is preferably a nonionic surfactant. When the organic acid is used as the antibacterial agent, since the drug aqueous solution becomes acidic, an anionic surfactant will have a low ionization rate and tend to have a lowered interface activity. In addition, since the water absorbent resin powder is disposed in the absorbent article, a cationic surfactant will form an ammonium salt with the water absorbent resin powder.

Examples of the nonionic surfactant include a polyoxyalkylene type and a polyhydric alcohol type. Examples of the polyoxyalkylene type include a polyoxyalkylene alkyl ether, a polyoxyalkylene fatty acid ester, a polyoxyalkylene polyhydric alcohol fatty acid ester, a polyoxyalkylene alkylphenyl ether, a polyoxyalkylene alkylamino ether, and a polyoxyethylene/propylene block polymer. Examples of the polyhydric alcohol type include a polyhydric alcohol fatty acid ester, a polyhydric alcohol alkyl ester ether, and a fatty acid dialkylol amide. As the nonionic surfactant, the polyoxyalkylene alkyl ether is preferable.

The HLB (Hydrophile Lipophile Balance) value of the nonionic surfactant is preferably 8 or more, more preferably 8.5 or more, and even more preferably 9 or more, and is preferably 15 or less, more preferably 13 or less, and even more preferably 12 or less. If the HLB value is 8 or more, the nonionic surfactant has better dispersibility in the drug aqueous solution, and if the HLB value is 15 or less, the drug aqueous solution has an enhanced permeation rate into the fiber assembly layer. In the present invention, the HLB value is calculated according to the following Griffin formula.

$$\text{HLB value} = 20 \times \{(\text{molecular weight of hydrophilic moiety})/(\text{total molecular weight})\}$$

The drug aqueous solution preferably contains the organic acid as the antibacterial agent and contains the nonionic surfactant having the HLB value of from 8 to 15 as the surfactant. The organic acid has a hydrophilic group, thus if the HLB value of the surfactant is from 8 to 15, the organic acid has further enhanced dispersibility.

The drug aqueous solution preferably contains a polyether-modified silicone, in addition to the antibacterial agent and/or deodorizer, and the surfactant. Inclusion of the polyether-modified silicone can suppress the formation of a liquid film between the fibers by the drug aqueous solution applied to the fiber assembly layer. Thus, the permeation of the drug aqueous solution into the fiber assembly layer can be further speeded up. The polyether-modified silicone is a compound having an alkylene oxide introduced in the backbone and/or side chain of silicone.

The HLB value of the polyether-modified silicone is preferably 7 or more, more preferably 8 or more, and is preferably 12 or less. If the HLB value is from 7 to 12, the polyether-modified silicone has better dispersibility in the drug aqueous solution and well cracks the liquid film between the fibers.

The method for spreading the drug aqueous solution on the fiber assembly layer is not particularly limited, for example, the drug aqueous solution can be sprayed on the fiber assembly layer. The amount of the drug aqueous solution can be suitably adjusted depending on the level of the drug, but 1 g to 30 g of the drug aqueous solution is usually used per 100 g of the fiber assembly layer.

The drug aqueous solution may be spread uniformly on the whole fiber assembly layer, or be spread nonuniformly on the fiber assembly layer. The amount per unit area, of the drug aqueous solution spread in the central region in the width direction of the fiber assembly layer is preferably higher than the amount per unit area of the drug aqueous solution spread in the regions of both edges in the width direction of the fiber assembly layer. The higher spreading amount in the central region in the width direction can increase the amount of the antibacterial agent and/or the deodorizer to be added in the urination position.

In addition, when the amount per unit area of the drug aqueous solution spread in the central region in the width direction of the fiber assembly layer is higher than the amount per unit area of the drug aqueous solution spread in the regions of both edges in the width direction of the fiber assembly layer, the amount per unit area of the fiber solvent spread in the central region in the width direction of the fiber assembly layer is preferably higher than the amount per unit area of the fiber solvent spread in the regions of both edges in the width direction of the fiber assembly layer in the second step. Specifically, it is preferable that the amount per unit area of the fiber solvent spread in the central region in the width direction of the fiber assembly layer is preferably higher than the amount per unit area of the fiber solvent spread in the regions of both edges in the width direction of the fiber assembly layer in the second step, and the amount per unit area of the drug aqueous solution spread in the central region in the width direction of the fiber assembly layer is higher than the amount per unit area of the drug aqueous solution spread in the regions of both edges in the width direction of the fiber assembly layer in the third step. The higher fixed degree of the fibers in the part where the drug amount is higher can suppress the retainment of the drug aqueous solution on the surface of the fiber assembly layer even if the amount of the drug aqueous solution is high.

(Fourth Step)

In the fourth step, the member including the water absorbent fiber is mounted on the surface where the drug aqueous solution has been spread of the fiber assembly layer.

The member includes the water absorbent fiber having higher hydrophilicity than the cellulose acetate fiber. Thus, if the member is mounted on the fiber assembly layer having the drug aqueous solution remained on the surface, the drug aqueous solution will migrate to the member. However, in the production method according to the present invention, the drug aqueous solution contains the surfactant, and the drug aqueous solution is taken into the fiber assembly layer immediately after the drug aqueous solution is spread on the fiber assembly layer. Thus, even if the member is mounted, migration of the drug aqueous solution to the member is suppressed.

Examples of the member include a tissue paper and a water absorbent layer. Thus, specific examples of the third step include a step of wrapping the fiber assembly layer with the tissue paper; a step of forming the water absorbent layer; and a step of disposing an absorbent body formed by wrapping the water absorbent layer with the tissue paper, on the fiber assembly layer.

EXAMPLES

Examples of the embodiment of the method for producing the absorbent article include the following embodiments 1 to 3.

Embodiment 1

A method for producing an absorbent article, comprising:
a first step of opening a cellulose acetate tow and collecting a cellulose acetate fiber to form a fiber assembly layer on a tissue paper;
a second step of spreading a fiber solvent on the fiber assembly layer and drying the fiber assembly layer;
a third step of spreading a drug aqueous solution containing an antibacterial agent and/or a deodorizer on the surface where the fiber solvent has been spread of the fiber assembly layer;
a fourth step of wrapping the fiber assembly layer with the tissue paper to form a wrapped body;
a fifth step of disposing the wrapped body on a back sheet;
a sixth step of disposing an absorbent body on the wrapped body; and
a seventh step of disposing a top sheet on the absorbent body.

Embodiment 2

A method for producing an absorbent article, comprising:
a first step of opening a cellulose acetate tow and collecting a cellulose acetate fiber to form a fiber assembly layer on a back sheet;
a second step of spreading a fiber solvent on the fiber assembly layer and drying the fiber assembly layer;
a third step of spreading a drug aqueous solution containing an antibacterial agent and/or a deodorizer on the surface where the fiber solvent has been spread of the fiber assembly layer;
a fourth step of wrapping a water absorbent layer with a tissue paper to form an absorbent body, and mounting the absorbent body on the surface where the drug aqueous solution has been spread of the fiber assembly layer; and a fifth step of disposing a top sheet on the absorbent body.

Embodiment 3

A method for producing an absorbent article, comprising:
a first step of opening a cellulose acetate tow and collecting a cellulose acetate fiber to form a fiber assembly layer on a back sheet;

a second step of spreading a fiber solvent on the fiber assembly layer and drying the fiber assembly layer;

a third step of spreading a drug aqueous solution containing an antibacterial agent and/or a deodorizer on the surface where the fiber solvent has been spread of the fiber assembly layer;

a fourth step of forming a water absorbent layer comprising a water absorbent resin powder and a pulp on the surface where the drug aqueous solution has been spread of the fiber assembly layer; and a fifth step of disposing a top sheet on the water absorbent layer.

REFERENCE SIGNS LIST

1: absorbent article, 2: top sheet, 3: back sheet, 5: absorbent body, 51: water absorbent layer, 52: first base material, 53: second base material, 6: wrapped body, 61: fiber assembly layer, 62: tissue paper, 7: side sheet, 8: rise elastic member

The invention claimed is:

1. A method for producing an absorbent article, wherein the absorbent article comprises: a fiber assembly layer including a cellulose acetate fiber, and a member including a water absorbent fiber and directly disposed on the fiber assembly layer, the method comprises:

a first step of opening a cellulose acetate tow and collecting a cellulose acetate fiber to form a fiber assembly layer;

a second step of spreading a fiber solvent on a surface of the fiber assembly layer and drying the fiber assembly layer;

a third step of spreading a drug aqueous solution containing an antibacterial agent and/or a deodorizer on the surface where the fiber solvent has been spread of the fiber assembly layer; and a fourth step of mounting the member on the surface where the drug aqueous solution has been spread of the fiber assembly layer.

2. The method for producing the absorbent article according to claim 1, wherein an amount per unit area of the fiber solvent spread in a central region in a width direction of the fiber assembly layer is higher than an amount per unit area of the fiber solvent spread in regions of both edges in the width direction of the fiber assembly layer in the second step, and an amount per unit area of the drug aqueous solution spread in the central region in the width direction of the fiber assembly layer is higher than an amount per unit area of the drug aqueous solution spread in the regions of both edges in the width direction of the fiber assembly layer in the third step.

3. The method for producing the absorbent article according to claim 1, wherein the fiber assembly layer is formed such that a density of a central region in a width direction of the fiber assembly layer is lower than a density of regions of both edges in the width direction of the fiber assembly layer in the first step, and an amount per unit area of the fiber solvent spread in the central region in the width direction of the fiber assembly layer is higher than an amount per unit area of the fiber solvent spread in the regions of both edges in the width direction of the fiber assembly layer in the second step.

4. The method for producing the absorbent article according to claim 1, wherein the antibacterial agent is an organic acid.

5. The method for producing the absorbent article according to claim 1, wherein the drug aqueous solution contains a nonionic surfactant having a HLB value of from 8 to 15.

6. The method for producing the absorbent article according to claim 1, wherein the drug aqueous solution further contains a polyether-modified silicone.

7. The method for producing the absorbent article according to claim 1, wherein the drug aqueous solution contains the antibacterial agent in an amount of 0.001 part by mass or more and 50 parts by mass or less with respect to 100 parts by mass of water.

8. The method for producing the absorbent article according to claim 1, wherein the drug aqueous solution contains the deodorizer in an amount of 0.01 part by mass or more and 50 parts by mass or less with respect to 100 parts by mass of water.

9. A method for producing an absorbent article, comprising:

a first step of opening a cellulose acetate tow and collecting a cellulose acetate fiber to form a fiber assembly layer on a back sheet;

a second step of spreading a fiber solvent on a surface of the fiber assembly layer and drying the fiber assembly layer;

a third step of spreading a drug aqueous solution containing an antibacterial agent and/or a deodorizer on the surface where the fiber solvent has been spread of the fiber assembly layer;

a fourth step of wrapping a water absorbent layer with a tissue paper to form an absorbent body, and mounting the absorbent body on the surface where the drug aqueous solution has been spread of the fiber assembly layer; and a fifth step of disposing a top sheet on the absorbent body.

10. The method for producing the absorbent article according to claim 9, wherein an amount per unit area of the fiber solvent spread in a central region in a width direction of the fiber assembly layer is higher than an amount per unit area of the fiber solvent spread in regions of both edges in the width direction of the fiber assembly layer in the second step, and an amount per unit area of the drug aqueous solution spread in the central region in the width direction of the fiber assembly layer is higher than an amount per unit area of the drug aqueous solution spread in the regions of both edges in the width direction of the fiber assembly layer in the third step.

11. The method for producing the absorbent article according to claim 9, wherein the fiber assembly layer is formed such that a density of a central region in a width direction of the fiber assembly layer is lower than a density of regions of both edges in the width direction of the fiber assembly layer in the first step, and an amount per unit area of the fiber solvent spread in the central region in the width direction of the fiber assembly layer is higher than an amount per unit area of the fiber solvent spread in the regions of both edges in the width direction of the fiber assembly layer in the second step.

12. The method for producing the absorbent article according to claim 9, wherein the antibacterial agent is an organic acid.

13. The method for producing the absorbent article according to claim 9, wherein the drug aqueous solution contains a nonionic surfactant having a HLB value of from 8 to 15.

14. The method for producing the absorbent article according to claim 9, wherein the drug aqueous solution further contains a polyether-modified silicone.

15. A method for producing an absorbent article, comprising:
- a first step of opening a cellulose acetate tow and collecting a cellulose acetate fiber to form a fiber assembly layer on a back sheet;
- a second step of spreading a fiber solvent on a surface of the fiber assembly layer and drying the fiber assembly layer;
- a third step of spreading a drug aqueous solution containing an antibacterial agent and/or a deodorizer on the surface where the fiber solvent has been spread of the fiber assembly layer;
- a fourth step of forming a water absorbent layer comprising a water absorbent resin powder and a pulp on the surface where the drug aqueous solution has been spread of the fiber assembly layer; and
- a fifth step of disposing a top sheet on the water absorbent layer.

16. The method for producing the absorbent article according to claim 15, wherein an amount per unit area of the fiber solvent spread in a central region in a width direction of the fiber assembly layer is higher than an amount per unit area of the fiber solvent spread in regions of both edges in the width direction of the fiber assembly layer in the second step, and
an amount per unit area of the drug aqueous solution spread in the central region in the width direction of the fiber assembly layer is higher than an amount per unit area of the drug aqueous solution spread in the regions of both edges in the width direction of the fiber assembly layer in the third step.

17. The method for producing the absorbent article according to claim 15, wherein the fiber assembly layer is formed such that a density of a central region in a width direction of the fiber assembly layer is lower than a density of regions of both edges in the width direction of the fiber assembly layer in the first step, and
an amount per unit area of the fiber solvent spread in the central region in the width direction of the fiber assembly layer is higher than an amount per unit area of the fiber solvent spread in the regions of both edges in the width direction of the fiber assembly layer in the second step.

18. The method for producing the absorbent article according to claim 15, wherein the antibacterial agent is an organic acid.

19. The method for producing the absorbent article according to claim 15, wherein the drug aqueous solution contains a nonionic surfactant having a HLB value of from 8 to 15.

20. The method for producing the absorbent article according to claim 15, wherein the drug aqueous solution further contains a polyether-modified silicone.

* * * * *